United States Patent
Wong et al.

(10) Patent No.: US 8,949,998 B2
(45) Date of Patent: Feb. 3, 2015

(54) METHOD AND SYSTEM FOR MAINTAINING DATA IN A SUBSTANTIATED STATE

(71) Applicant: Medidata Solutions, Inc., New York, NY (US)

(72) Inventors: Isaac Wong, New York, NY (US); Johnlouis Petitbon, Brooklyn, NY (US); Benjamin Young, Manlius, NY (US); Matthew Szenher, New York, NY (US); Andrew Newbigging, London (GB)

(73) Assignee: Medidata Solutions, Inc., New York, NY (US)

( * ) Notice: Subject to any disclaimer, the term of this patent is extended or adjusted under 35 U.S.C. 154(b) by 0 days.

(21) Appl. No.: 13/933,122

(22) Filed: Jul. 1, 2013

(65) Prior Publication Data
US 2015/0007271 A1    Jan. 1, 2015

(51) Int. Cl.
*H04L 29/06* (2006.01)
*H04L 29/08* (2006.01)

(52) U.S. Cl.
CPC ............... *H04L 67/10* (2013.01); *H04L 63/08* (2013.01)
USPC ........................................................ 726/26

(58) Field of Classification Search
CPC ...................................................... H04L 67/10
USPC ................................................... 726/26, 27
See application file for complete search history.

(56) References Cited

U.S. PATENT DOCUMENTS

| | | | |
|---|---|---|---|
| 6,557,102 B1 * | 4/2003 | Wong et al. | 713/176 |
| 6,671,804 B1 * | 12/2003 | Kent | 713/175 |
| 8,130,768 B1 * | 3/2012 | Ahrens et al. | 370/401 |
| 2002/0059425 A1 | 5/2002 | Belfiore et al. | |
| 2003/0191843 A1 * | 10/2003 | Balissat et al. | 709/227 |
| 2005/0044197 A1 | 2/2005 | Lai | |
| 2005/0202392 A1 | 9/2005 | Allen et al. | |
| 2007/0107059 A1 * | 5/2007 | Chasin et al. | 726/23 |
| 2012/0159643 A1 | 6/2012 | Bradley et al. | |
| 2012/0246124 A1 * | 9/2012 | Arasaratnam | 707/692 |

FOREIGN PATENT DOCUMENTS

WO    03-046748 A1    6/2003

OTHER PUBLICATIONS

The International Search Report and the Written Opinion of the International Searching Authority, PCT/US2014/044789, Oct. 17, 2014.

* cited by examiner

*Primary Examiner* — Jason K Gee
(74) *Attorney, Agent, or Firm* — Steptoe & Johnson LLP; Robert Greenfeld

(57) ABSTRACT

A method for maintaining data in a substantiated state includes executing one or more services on the data message at a first node, annotating the message header with the services executed at the first node, transmitting the data message over a data network, and receiving the annotated data message at a second node. The annotation corresponds to the services executed at the first node, and the annotated data is extractable from the header for the execution of services at the second node. A system for maintaining data in a substantiated state is also described.

15 Claims, 2 Drawing Sheets

METHOD AND SYSTEM FOR MAINTAINING DATA IN A SUBSTANTIATED STATE

BACKGROUND

In a distributed network, such as the Internet, data may travel from point-to-point or node-to-node. The data may often be substantiated at those points or nodes to ensure, for example, that messages containing the data are correct and accurate or that the messages' history is known. But data in transit within the network may not be substantiated, which may require duplicative and wasteful use of processing resources at subsequent points or nodes.

Figure 1:
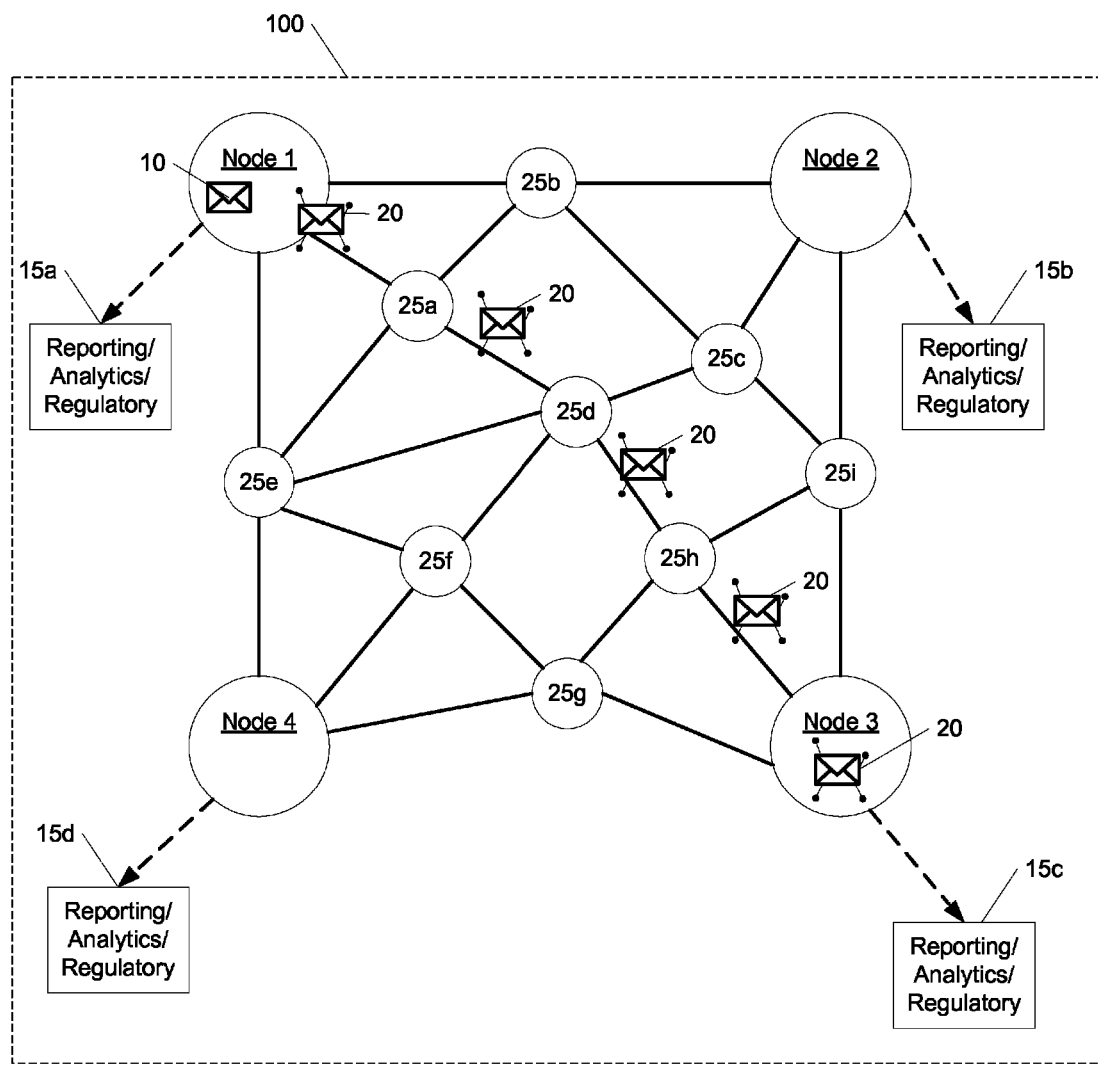
FIG. 1 is a schematic diagram of a system for maintaining data in a substantiated state, according to one embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

The present invention may allow data (also referred to herein as "data messages") to be maintained in a substantiated state while in transit between substantiated nodes of a distributed network, such as the Internet. These data messages may include, but are not limited to, a message body and a message header. The message header may include, but is not limited to, information (annotations) used to substantiate the message. A message may be substantiated for a variety of reasons, including but not limited to confirming or re-creating the status of the data message when the message is received at a subsequent point or node. Substantiation of the data message or re-creation of the data message's substantiated state may not need to be performed at each node, thus freeing up computational resources.

Embodiments of the present invention may be used in a variety of applications. For example, the techniques disclosed herein may be used in environments in which data may be substantiated at various transmission points of a data network, including nodes or places in which services reside. Data related to clinical drug or device trials (or studies) may be an example of a type of data that may need to be substantiated in order to satisfy requirements issued by, for example, a regulatory agency such as the United States Food and Drug Administration (FDA) or its foreign counterpart agencies. These applications are not intended to be limiting, and the present invention may be utilized in any application requiring substantiation of data.

Reference is now made to FIG. 1, which is a schematic diagram of a system 100 for maintaining data in a substantiated state, according to one embodiment of the present invention. In FIG. 1, Nodes 1-4 may be resources such as systems or software applications that execute, operate on, or provide data in response to a message or other data 10; Nodes 1-4 may also be services, as described further herein. In one non-limiting example, the application in Node 1 may be an electronic data capture (EDC) program that captures data from a clinical drug trial; the application in Node 2 may be a medical or clinical coding system; the application in Node 3 may be a clinical trial management system (CTMS) that uses the data from the EDC program in Node 1 plus the coding results from Node 2; and the application in Node 4 may be a clinical design program. As will be appreciated by one of skill in the art, execution of a resource or service at a node may be local, e.g., occurring at a local server, or may be executed at remote servers, e.g., by application programming interface (API) calls, publication-subscription, etc., and resources and services may be executed on the same or different servers, or across servers. Execution of the services in Nodes 1-4 may substantiate message 10 when it is received by, and operated on by services at, subsequent nodes. Boxes 15a-15d represent various resources that may operate on the data at the nodes once the data is substantiated. These resources include, but are not limited to, reporting data to another node, performing analytics on the message body, or providing information to a regulatory authority. Additional resources at subsequent nodes may also include any clinical application or system, including but not limited to a protocol design service, a medical coding service, an EDC service, or a safety reporting service.

In a distributed network such as the Internet, nodes may exist at various geographical locations, such as Denver, Dallas, Philadelphia, and Boston, and data messages may need to be transferred between these nodes. In one embodiment, routing points 25a-i may be located between each of the nodes. The routing points may direct a message from one node to another node using various types of network routing, including but not limited to standard IP-based routing (e.g., TCP/IP).

Although data or messages may originate at any node, FIG. 1 illustrates that message 10 may originate in Node 1. According to one embodiment, the message may be annotated in the originating node with a variety of information, including but not limited to the results of one or more services that operated on, or executed based on, the message. Such an annotated message may be substantiated, as depicted as data message 20 (shown by the connections to the message). In the embodiment of FIG. 1, data message 20 is being transmitted from Node 1 toward Node 3 (and one of skill in the art will understand that the data message may be transmitted from any node to any other node). According to one embodiment, and as illustrated in FIG. 1, data message 20 may remain in a substantiated state while it is in transit.

Figure 2:
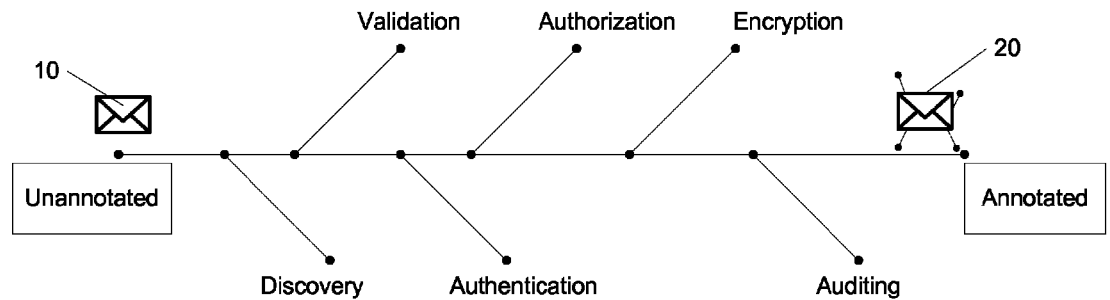
FIG. 2 is a schematic diagram illustrating the annotation of a data message with services, according to one embodiment of the present invention.

FIG. 2 is a schematic diagram illustrating the annotation of data message 10 with the results of executed services, according to one embodiment of the present invention. In this embodiment, the message is considered to be in a substantiated state. Data that is substantiated may be annotated with several attributes or may encounter various services. These attributes or services include, but are not limited to, discovery, validation, authentication, authorization, encryption, and auditing services. Attributes of those services may provide, for example, information about the message, such as information that may be viewed as the "who," "what," "where," etc., of the data of the message.

According to one embodiment, a discovery service may operate on the message to indicate "where" the message came from, to determine the network location of the message's destination at the time it was sent from Node 1, and/or to determine the location of resources that may be utilized to operate with or on the message. For example, if a message contains information concerning an update for a clinical subject, the discovery service may determine the location of a resource such as an EDC system, which resource may operate on the message to update subject clinical information. Advantageously, the use of a discovery service allows for a distributed system in which the addresses, such as IP addresses, of services or resources are not hard-coded, but may be calculated through HTTP (hypertext transfer protocol) calls or similar calls. It will be appreciated that calls to a discovery service may be made in the event that an address changes during the time it takes for a message to be delivered within the distributed system.

The validation service may also, or alternatively, operate on the message to indicate "what" information is in the message body by verifying that the transmitted message includes a guarantee that the sending node, or an original sending node, successfully fulfilled an industry-standard code validation (e.g., source code or object code) process. The validation service may also verify that the sending or receiving node, service, or resource—at the moment the data message was transmitted—is running the exact source code that was validated and proven to work per its specific validation requirements. In the clinical data environment, an "industry standard validation process" may be 21 CFR Part 11 or HIPAA (Health Insurance Portability and Accountability Act) requirements, and the validation service may include services that address data privacy or HIPAA requirements with regard to data messages. In one embodiment of the present invention, the validation service may operate to confirm that a human applied an electronic or digital signature to the code executed at a sending node. Application of such an electronic or digital signature may serve to confirm that a human was responsible for verifying that the functionality of the code, currently running, was validated against regulatory standards, e.g., that 21 CFR Part 11-compliant code was utilized at the sending node. In another embodiment, electronic or digital signatures may be provided by operation of validation services that do not require human intervention. In still another embodiment of the present invention, the validation service may operate on the message to perform data validation, that is to provide specific validation of critical data such as ensuring the uniqueness of a clinical study's protocol identifier, or for critical tasks such as clinical data locking or subject unblinding. The validation service may provide guarantees about system 100 as a whole, described further herein.

The authentication service may also, or alternatively, operate on the message to indicate "who" (e.g., a person, service, or resource) transmitted the message to ensure that the message can be trusted (i.e., that it comes from an authenticated source). Annotations reflecting execution of the authentication service at a first node may allow any subsequent destination node to verify the authenticity of the first node, that is, to verify the authenticity of any node where the message has been, and the integrity of the data exchange. Examples of authentication services known to those of skill in the art include Kerberos, RADIUS, and services utilizing standards such as hash-based message authentication codes (HMAC) (also called "keyed-hash message authentication codes"), which may use cryptographic hash functions such as MD5, SHA-1, and SHA-256.

The authorization service may also, or alternatively, operate on the message to indicate "what" type of access the person, resource, service, or node transmitting the message has and what the message can do or where it can go. For example, within a clinical study environment, authorization may involve access to a specific clinical study or a specific clinical study site, whether a person can access the record of a specific study subject, and the level of access someone may have to the data generated by the study. Execution of an authorization service, alone or in conjunction with an authentication service, helps to demonstrate the importance of the present invention for clinical resources executed within a multi-tenant architecture, such as single instance multi-tenancy (SIMT). In such multi-tenant systems, e.g., cloud-based deployment of software applications, a single database and/or single application service running on a single, dedicated application server may be used by multiple customers. Access to the database and/or application server must therefore be securely and accountably verified for each user. Execution of the services of the present invention, including authentication and authorization, serve to provide assurances that the resources at each node are correctly and verifiably accessed.

In one embodiment, an encryption service may operate on a message to encrypt the message according to a protocol, such as AES-256 (Advanced Encryption Standard), or other industry-standard encryption protocols, including public/private key encryption. For example, Node 1 may have both a public and private key, and encrypt a message with the private key, which Node 2 then unencrypts by checking an agreed-upon algorithm with the public key sent to it by Node 1.

In one embodiment, an auditing service may operate on a message to capture an audit trail for each message. An audit trail is a record of the transformations the data has experienced, and a review of an audit trail may serve to verify that any data transformations were correctly executed. Using an audit trail, one may reconstruct a valid and accurate timeline of a series of actions that took place in a distributed system composed of independent agents based on the notion of causality. As such, auditing may be used to satisfy clinical regulatory standards. An audit trail is typically created upon completion of a data transformation at a given node of a network by creating or updating records in a database. A message may also be operated on and annotated with other attributes or services, or not be operated on and annotated with all attributes or services described herein, and the order of the attributes or services in FIG. 2 is not critical.

In one embodiment of the present invention, the first node at which the services described herein are executed may be viewed as a "gateway" between unknown or unsubstantiated transmitting nodes and any subsequent known or substantiated nodes. In such an embodiment, the gateway node may serve as a first node beyond which services executed at that first node do not need to be re-executed for access to known resources. For example, a gateway node at which services are executed may be viewed as a means to incorporate the receipt of data (or a request for data) from an unknown source with the execution of known, trusted resources (e.g., clinical applications) residing at the gateway node or beyond, e.g., any subsequent receiving nodes.

Figure 3:
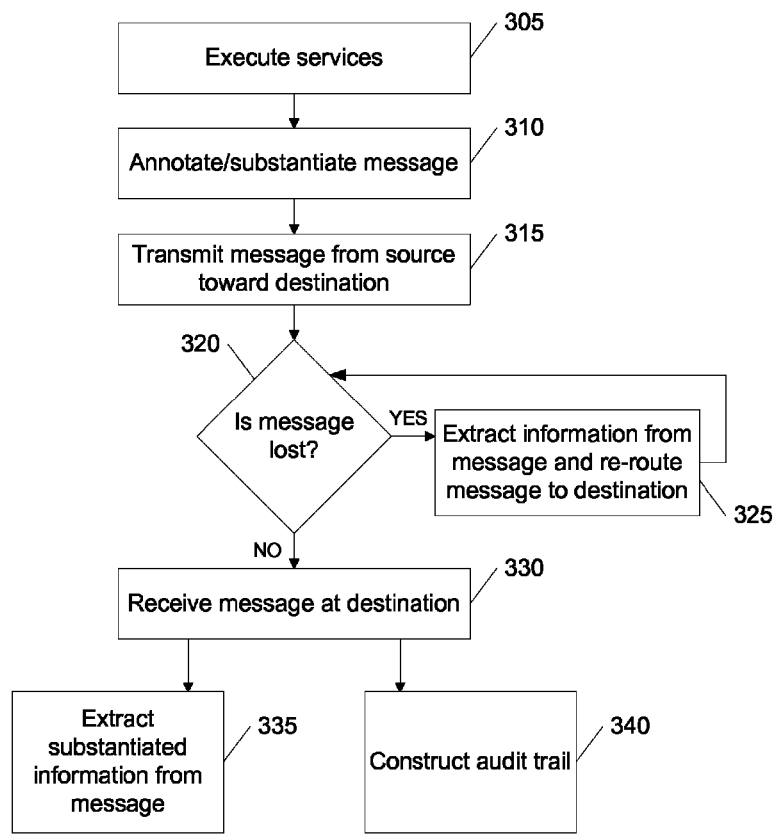
FIG. 3 is a flowchart illustrating the steps associated with one embodiment of the present invention.

In the present invention, maintaining data messages in a substantiated state may allow audit trails to be generated using the information maintained with the message header without having to rely on re-executing services to substantiate the messages at subsequent nodes, or without having to delve into the message body. FIG. 3 is a flowchart illustrating the steps of an embodiment of the present invention. In operation 305, services discussed with reference to FIG. 2 may be executed to operate on a data message. For example, a message at a first node may be operated on by one or more of discovery, validation, authentication, authorization, encryption, and/or auditing services, or other services. In operation 310, substantiation information may be added to the header of the message, that is, the message header may be annotated to indicate the results of the operations of the services executed in operation 305. Such annotations may include yes/no flags, i.e., calculations that a service has been successfully completed, tokens or other hypermedia resulting from the operation of services such as discovery, tokens or other pointers to certificates associated with a validation service, transaction IDs, electronic signatures, or digital certificates. The upshot of annotations of the execution of the one or more services is the secure, accountable execution of system 100 as a whole.

In operation 315, the data message may be transmitted from a first node (source) to a second node (destination), during which the message retains its substantiated information. Because the message is substantiated, even if the message becomes lost, as may occur as a result of faults with HTTP calls or proxies in the TCP/IP and DNS communications process or the re-location of a resource, the message may be directed to its destination. Thus, operation 320, which may occur at any place in transit along a network such as routing points 25a-i or at any node, asks whether the message is lost. If so, in operation 325, the substantiated information may be extracted from the message directly in order to determine the message's destination. The process returns to operation 320 and asks whether the message is lost. The answer to the operation 320 is NO when the message is received at the destination in operation 330. At that point, in operation 335, the substantiated information may be extracted from the message directly, rather than needing to execute services again, as in prior systems. In addition, once the message is received at the destination, an audit trail may be constructed in operation 340. Besides the operations shown in FIG. 3, other operations or series of operations are contemplated to maintain data in a substantiated state. For example, some but not all of the services described with regard to FIG. 2 may be employed at a first node, e.g., Node 1; instead, some such services may occur at a first node, and others occur at later nodes. In more detail, some nodes may execute services to check a data message only for validation information, others for authorization information, and still others for discovery information, as described with regard to a lost message. Moreover, the actual order of the operations in the flowchart is not intended to be limiting, and the operations may be performed in any practical order.

One embodiment of the present invention may use means for annotating a substantiated data message in addition to annotating a message header. For example, a transaction ID may be substituted for annotations within a message header, or may be written to an audit database. In further detail, a transaction ID may act as a reference to all information relating to transactions that operated on or as a result of a message at a node, and that transaction ID may be stored in a message header, or may be retrievable at nodes subsequent to a node at which the message was substantiated from a database storing audits which contain the transaction ID.

It should be understood that annotation of a data message with executed services, including those described above, may include annotating only the message header. As described herein, where the message header has been annotated to include the information used to substantiate the message, the data message's (or transaction ID's) substantiated status can be verified by examining the header rather than the message body itself, thereby freeing up computational resources.

In one embodiment, the substantiation of a message with some services may include annotating, or changing, the data of the message body as well as the message header. For example, a message body may include data that is operational by one person or service, and other data that is operational by another person or service. In such a case of overlapping authorization or permissions, for example, an encryption service and/or an authorization service may operate on the body of the message as well as the header, by creating one or more "cloaks" or layers of the data message exposed to the transport layer. An inner cloak or layer may be contained within the message body and be substantiated by some services, such as a validation service or an encryption service, where an outer cloak or layer may be contained within the message header and may be substantiated by overlapping or additional services than those which operated in the inner cloak or layer, such as an authorization or an encryption service.

As another example of the substantiation of a message with services that include annotating, or changing, data within a message body, according to one embodiment, a validation service may remove or hide certain data contained within the message body. For example, in order to meet regulations concerning data or patient privacy, geolocation information contained within a message body may be removed, hidden, or rendered inaccessible when the data message travels into or outside of certain geographic areas. In such instances, the message header may also be annotated to reflect the change to the validated status of the message body.

An analogy may be illustrative of aspects of the present invention. The data message may be likened to a package that is being delivered. The sender is considered a substantiated source, for example, a mail-order business. The conventional way of sending such a package is to place the destination address on the front. When the package arrives at the destination, the recipient must open up the package (which may be difficult to do) to determine what is inside and where it came from and what the contents of the package mean (for example, what the recipient is supposed to do with the contents of the package). If there are many packages, it may be difficult for the recipient to keep track of which contents came from which source, which may be important for auditing purposes and/or may be a burden on operational resources. It is also possible that the package may get lost if, for example, the address on the front gets erased or mutilated. In that case, the package may never get to the destination.

In contrast, as an analogy to embodiments of the invention, the package is sent from a substantiated source, but the information about the package (what is inside, where it came from, and what the contents of the package mean) is provided with the package (possibly in an encrypted format) so that such information can be determined without going through the difficulty of opening the package. The recipient can keep track of the information related to each message by retaining the packing information. If the package is lost along the way, whoever finds the package can determine (so long as the relevant encryption information is known) the intended destination without opening up the package.

One of skill in the art will understand that the present invention is not limited to the above analogy. Indeed, it is contemplated that the present invention may encompass not just one message, but numerous messages, all being transmitted from sources to destinations and all needing to be tracked. Their journeys from source to destination do not always follow the shortest path, and once the messages leave the source node, there may be little control over how the message will actually arrive at the destination.

One embodiment of the present invention is directed to the transport layer of the seven-layer Open Systems Interconnection (OSI) model, and may also be implemented via middleware. For example, referring back to FIG. 1, in prior systems, data messages are safe (i.e., substantiated and cannot be lost) when they reside at one of the four nodes shown, but once the messages leave the nodes, they are at the mercy of the transmission network, such as the Internet, and there are no guarantees that any particular message will arrive at its destination intact, or without having been tampered with or otherwise altered. In contrast, in the system of the invention, once each message is operated on and substantiated by services and such executed services are annotated in the message, the whole system 100 becomes substantiated and the messages' integrity remains intact so long as the messages remain within system 100, even if the messages are somewhere between the geographical locations of the nodes (e.g., Denver, Dallas, Philadelphia, and Boston, as described in the above embodiment). Thus, while a data message is anywhere within system 100, any of the resources represented by boxes 15a-15d could be performed on the message, whether the message has arrived at a subsequent node, or is en route from one node to another.

In an embodiment of the invention, by maintaining substantiation information with the message header, an audit trail can be recreated and audits may be performed using fewer computational resources than if the message were transmitted without such information. Reporting of events can occur more quickly and easily, too. Moreover, as the amount of data transferred increases, the ease of creating an audit trail scales with the amount of data, whereas without maintaining substantiated information, increasing the amount of data transferred may exponentially increase the effort it takes to create such an audit trail. In addition, if any specific message were to become lost—or tampered with, in terms of encryption—in transit from one node to another, by looking at the substantiation information maintained with the message, such data could be routed to the proper node (or tampering would be detected).

Embodiments of the present invention have been described in the context of a distributed network. Examples of such a network include the Internet, an intranet, a wide area network (WAN), or local area network (LAN), and could also include the public switched telephone network (PSTN) or a private telephone network. In some cases, the connections between nodes may occur within a computer or other type of closed system. The services executed to substantiate messages may be used as part of a software application that may run on a computer or that may be part of software as a service (SaaS) or a service-oriented architecture (SOA). The services may also be offered as a cloud-based service or hosted service, which may be accessed through a standard web service API or over a restful API.

Aspects of the present invention may be embodied in the form of a system, a computer program product, or a method. Similarly, aspects of the present invention may be embodied as hardware, software or a combination of both. Aspects of the present invention may be embodied as a computer program product saved on one or more computer-readable media in the form of computer-readable program code embodied thereon.

For example, the computer-readable medium may be a computer-readable signal medium or a computer-readable storage medium. A computer-readable storage medium may be, for example, an electronic, optical, magnetic, electromagnetic, infrared, or semiconductor system, apparatus, or device, or any combination thereof.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device.

Computer program code in embodiments of the present invention may be written in any suitable programming language. The program code may execute on a single computer, or on a plurality of computers. The computer may include a processing unit in communication with a computer-usable medium, wherein the computer-usable medium contains a set of instructions, and wherein the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A computer-implemented method for transmitting a data message in a network, the data message having a header, the method comprising:
   executing at a first node a validation service and an auditing service that operate on the data message, wherein:
      the validation service guarantees that software code operating at the first node successfully fulfilled a regulatory standard software code validation process; and
      the auditing service captures an audit trail for the data message in compliance with the regulatory standard;
   generating substantiation information comprising the results of the execution of the validation and auditing services;
   substantiating the data message by adding the substantiation information to the header at the first node;
   transmitting the substantiated data message over the network;
   receiving the substantiated data message at a second node; and
   extracting at the second node the substantiation information from the header to verify that the data message remains substantiated.

2. The method of claim 1, wherein the data message includes data related to a clinical trial or clinical study.

3. The method of claim 2, wherein a discovery service, an authentication service, an authorization service, and an encryption service are also executed at the first node and operate on the data message.

4. The method of claim 3, wherein if the data message is lost in transmission in the data network, the data message is re-routed based on the substantiation information in the header.

5. The method of claim 2, wherein the validation service provides compliance with 21 CFR Part 11 requirements.

6. The method of claim 1, wherein the validation service provides compliance with HIPAA requirements.

7. A computer-based system for maintaining data in a substantiated state, comprising:
   a distributed data network having at least a first node and a second node; and a processor located at each node,
wherein the processor at the first node:
- executes a validation service and an auditing service that operate on a data message, the data message having a header;
- generates substantiation information comprising the results of the execution of the validation and auditing services; and
- substantiates the data message by adding the substantiation information to the header, and wherein:
- the validation service is configured to guarantee that software code operating at the first node successfully fulfilled a regulatory standard software code validation process; and
- the auditing service is configured to capture an audit trail for the message in compliance with the regulatory standard.

8. The system of claim 7, wherein the data message includes data related to a clinical trial or clinical study.

9. The system of claim 8, wherein the validation service guarantees compliance with 21 CFR Part 11 requirements or HIPAA requirements.

10. The system of claim 7, wherein the processor at the first node further executes a discovery service, an authentication service, an authorization service, and an encryption service that operate on the data message.

11. The system of claim 10, wherein the substantiation information from the discovery service is related to the origin of the data message.

12. The system of claim 10, wherein the authentication service authenticates the data message to determine who transmitted the message.

13. The system of claim 10, wherein the authorization service authorizes the transmission of the message based on access rights.

14. The system of claim 7, wherein the processor at the first node transmits the substantiated data message over the network.

15. The system of claim 14, wherein the processor at the second node receives the substantiated data message and extracts the substantiation information from the header to verify that the data message remains substantiated.

* * * * *